(12) United States Patent
Denham et al.

(10) Patent No.: US 11,504,137 B2
(45) Date of Patent: Nov. 22, 2022

(54) BONE CUT GUIDE APPARATUS AND METHOD

(71) Applicant: NEXTREMITY SOLUTIONS, INC., Warsaw, IN (US)

(72) Inventors: Gregory J. Denham, Warsaw, IN (US); Ryan Schlotterback, Warsaw, IN (US)

(73) Assignee: MEDARTIS AG, Basel (CH)

( * ) Notice: Subject to any disclaimer, the term of this patent is extended or adjusted under 35 U.S.C. 154(b) by 143 days.

(21) Appl. No.: 17/022,761

(22) Filed: Sep. 16, 2020

(65) Prior Publication Data
US 2021/0077131 A1    Mar. 18, 2021

Related U.S. Application Data

(60) Provisional application No. 62/900,920, filed on Sep. 16, 2019, provisional application No. 62/991,879, filed on Mar. 19, 2020, provisional application No. 63/015,052, filed on Apr. 24, 2020.

(51) Int. Cl.
*A61B 17/17* (2006.01)
*A61B 17/15* (2006.01)
*A61B 17/68* (2006.01)

(52) U.S. Cl.
CPC .......... *A61B 17/15* (2013.01); *A61B 17/1782* (2016.11); *A61B 17/1796* (2013.01); *A61B 2017/681* (2013.01)

(58) Field of Classification Search
CPC .. A61B 17/1782; A61B 17/15; A61B 17/1796
See application file for complete search history.

(56) References Cited

U.S. PATENT DOCUMENTS

| 4,565,191 A | * | 1/1986 | Slocum | A61B 17/15 606/87 |
| 4,952,214 A | * | 8/1990 | Comparetto | A61B 17/152 606/82 |
| 5,366,457 A | * | 11/1994 | McGuire | A61B 17/1677 606/86 R |
| 5,843,085 A | * | 12/1998 | Graser | A61B 17/15 606/87 |
| 7,967,823 B2 | * | 6/2011 | Ammann | A61B 17/1675 606/88 |
| 8,083,746 B2 | * | 12/2011 | Novak | A61B 17/8866 606/88 |

(Continued)

FOREIGN PATENT DOCUMENTS

| EP | 1508316 A1 | 2/2005 |
| GB | 2583572 A | 11/2020 |

OTHER PUBLICATIONS

UKIPO Search Report dated Feb. 23, 2021.

*Primary Examiner* — Christian A Sevilla
(74) *Attorney, Agent, or Firm* — Heslin Rothenberg Farley & Mesiti P.C.; Victor A. Cardona, Esq.

(57) ABSTRACT

A bone cut guide includes a first portion having a first cut slot and having an aperture for receiving a wire to connect the first portion to a first bone. A second portion has a second cut slot and a second aperture for receiving a second wire to connect the second portion to a second bone. The first portion and the second portion are movably connected to each other to allow the first bone and the second bone to move relative to each other.

11 Claims, 9 Drawing Sheets

(56) References Cited

U.S. PATENT DOCUMENTS

2016/0235414 A1    8/2016  Hatch et al.
2017/0079669 A1    3/2017  Bays et al.
2019/0336140 A1*  11/2019  Dacosta ................. A61B 17/15

* cited by examiner

BONE CUT GUIDE APPARATUS AND METHOD

CROSS-REFERENCE TO RELATED APPLICATIONS

The present application claims priority to U.S. Provisional Application No. 62/900,920 filed on Sep. 16, 2019, U.S. Provisional Application No. 62/991,879 filed Mar. 19, 2020, and U.S. Provisional Application No. 63/015,052 filed Apr. 24, 2020, which are incorporated herein by reference in their entirety.

BACKGROUND

Field of the Invention

This application relates to apparatuses, devices, and methods for adjusting and joining bones.

Description of the Related Art

Hallux valgus is the medical term for a bunion. The first tarsal-metatarsal (TMT) joint is an important joint at the inner part of the middle of the foot. The two bones that meet to form this joint are the first metatarsal and medial cuneiform bones. When this joint has too much looseness or movement, the condition is known as hypermobility or instability. When this joint becomes hypermobile, the first metatarsal moves too much in one direction and the first toe compensates by moving too much in the other direction. When this happens, a bunion develops.

The bunion is a disease of the joint and soft tissue. A bunion deformity or hallux abducto valgus deformity results from the big toe deviating laterally toward the patient's smallest toe. Due to the lateral movement of the big toe, the first metatarsal bone angles toward the smaller toes on the patient's foot causing the first metatarsal bone to move out of alignment. Bunions may become irritating and, in some cases, very painful during walking and other weight bearing activities. Bunions may also be painful and debilitating condition that prevents wearing shoes. Genetics and poor shoe design are the causes. The angle between the metatarsal of the second digit is a means to quantify the degree of deformity.

Painful bunions are corrected by surgical soft tissue management and surgical bone reforming. The first metatarsal is corrected by sectioning it with a saw and moving the head laterally. There are numerous cut locations from the proximal to distal regions, namely the chevron, Ludloff, Mau and proximal. The bones are shifted, and held in place with screws, staples or plates. Sometimes adjacent joints are fused to stabilize the reconstruction.

The Lapidus procedure is a type of fusion of the first TMT joint that decreases the movement of that joint and straightens out the first metatarsal and toe, so the Lapidus procedure treats bunions caused by first TMT joint hypermobility.

The goal of the Lapidus procedure is to surgically treat hallux valgus that is caused by first TMT joint hypermobility. An orthopedic foot and ankle surgeon realigns to a normal toe shape by placing the first metatarsal straight with the medial cuneiform bone and locking or fusing these two bones together. When the first TMT joint is fused, the first metatarsal will not move abnormally. This will allow the first toe to stay straight and prevent the bunion from coming back.

There is thus a need for alternative designs for systems and methods for cutting and joining two bone pieces, including implants that fix the two bone pieces, particularly designs that allow adjustment of the angle of flexion between the two bones.

SUMMARY OF THE INVENTION

The present invention provides, in a first aspect, a bone cut guide which includes a first portion having a first cut slot and having an aperture for receiving a wire to connect the first portion to a first bone. A second portion has a second cut slot and a second aperture for receiving a second wire to connect the second portion to a second bone. The first portion and the second portion are movably connected to each other to allow the first bone and the second bone to move relative to each other.

The present invention provides, in a second aspect, a method for use in aligning bones which includes inserting a joint arm of a guide between a first bone and a second bone. A first wire is inserted through a guide aperture of the guide into the first bone. The guide is removed and a first portion of a bone cut guide is attached to the first bone by receiving the wire in a first aperture of the bone cut guide and inserting the first wire in the first bone. A second portion of the bone cut guide is attached to a second bone by receiving a wire in a first aperture of the bone cut guide and inserting the second wire in the second bone.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

Corresponding reference characters indicate corresponding parts throughout the several views. The exemplary embodiments set forth herein are not to be construed as limiting the scope of the invention in any manner.

DETAILED DESCRIPTION OF THE EMBODIMENTS

Figure 1:
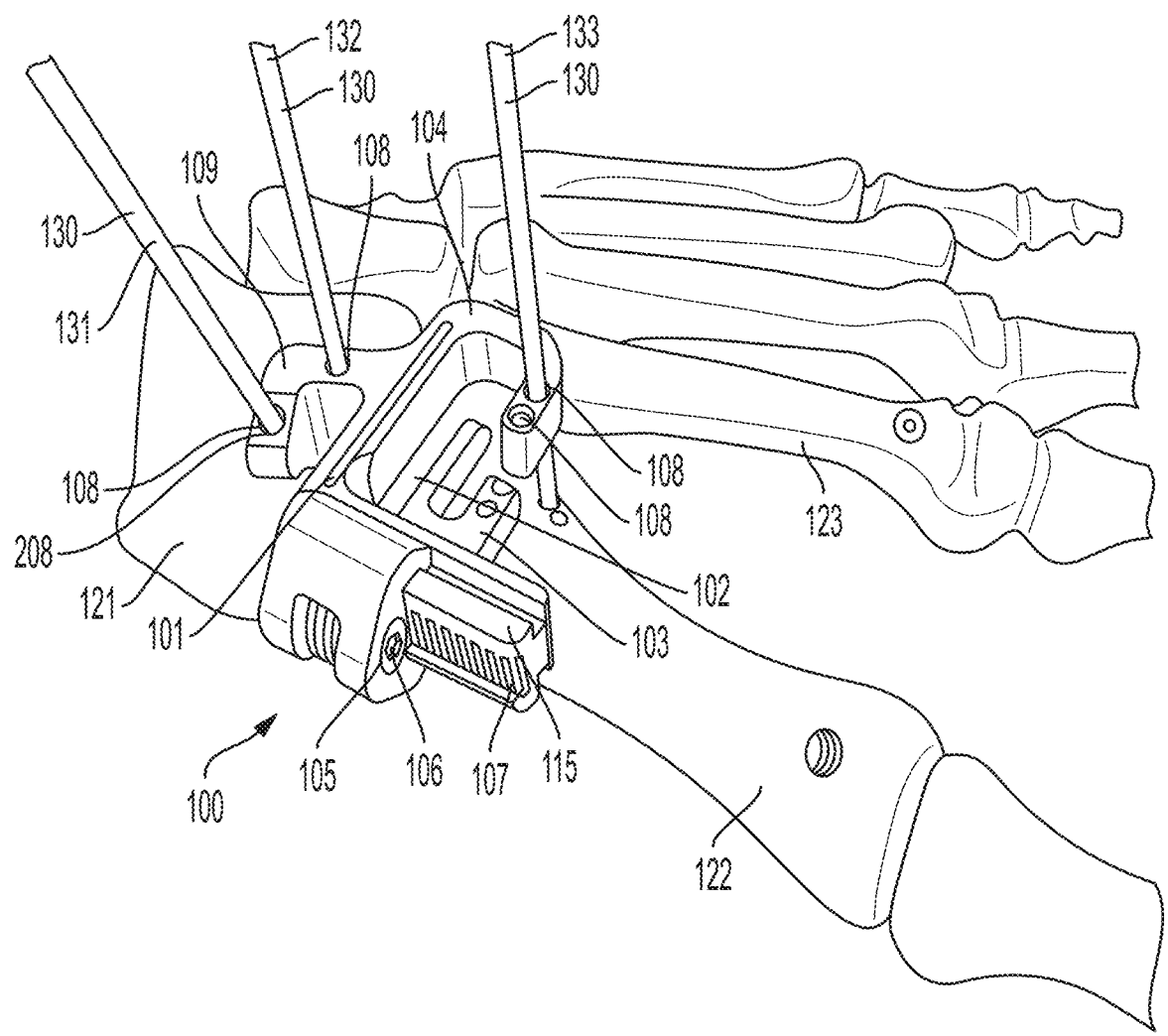
FIG. 1 is a perspective view of an embodiment of a cut guide, in accordance with an aspect of the present invention.

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for cutting tools for orthopedic surgery involving a foot or lower extremities. However, those possessing an ordinary level of skill in the relevant art will appreciate that other extremities, joints, and parts of the musculoskeletal system are suitable for use with the foregoing systems, methods and apparatuses. Likewise, the various figures, steps, procedures and work-flows are presented only as an example and in no way limit the systems, methods or apparatuses described to performing their respective tasks or outcomes in different time-frames or orders. The teachings of the present invention may be applied to any orthopedic surgery, such as on the hand as well as other upper and lower extremities and may be implemented in other treatments sites that have similar anatomical considerations.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As depicted in FIGS. 1 and 4-11, a cut guide 100 is connected to a first metatarsal bone 122 and a medial cuneiform bone 121 by a plurality of landmark guide wires or k-wires 130 inserted through a plurality of holes or bores 108 extending through cut guide 100. Cut guide positioning is depicted in relation to a second metatarsal bone 123. Cut guide 100 has a first member or cut guide body 104, a second member or metatarsal cutting fixture or mobile metatarsal cutting portion 103, an arm 109 and a compress-distraction fixture 105. Compression-distraction fixture 105 extends from second member 103 and engages with first member 104 along a linear track 115, with linear track 115 connected to first member 104. Linear track 115 has a threaded rack 107 on a lateral face and a track groove 112. Compression-distraction fixture 105 has a power screw or metatarsal adjustment screw 106. When power screw 106 is engaged and turned by screwdriver 250, compression-distraction fixture 105 is translatable movable along threaded rack 107 and within track groove 112.

Further referring to FIGS. 1 and 4-11, first member 104 has a first cut slot or proximal cuneiform cutting slot 101 and second member 103 has a second cut slot or distal metatarsal cutting slot 102. Proximal cuneiform cutting slot 101 is elongated in the medial-lateral direction and narrow in the anterior-posterior direction. Proximal cuneiform cutting slot 101 extends through first member 104 in the dorsal-plantar direction. Distal metatarsal cutting slot 102 is a "U" shaped slot, elongated in the medial-lateral direction and narrow in the anterior-posterior direction. Distal metatarsal cutting slot 102 extends through second member 103 in the dorsal-plantar direction. Proximal cuneiform cutting slot 101 and distal metatarsal cutting slot 102 are parallel.

With continued reference to FIGS. 1 and 4-11, second member 103 and compression-distraction fixture 105 are connected and therefore both are translated, moving in an anterior-posterior direction relative to first member 104, when power screw 106 is turned. Proximal cuneiform cutting slot 101 and distal metatarsal cutting slot 102 remain parallel under, and after, such translation.

Figure 2:
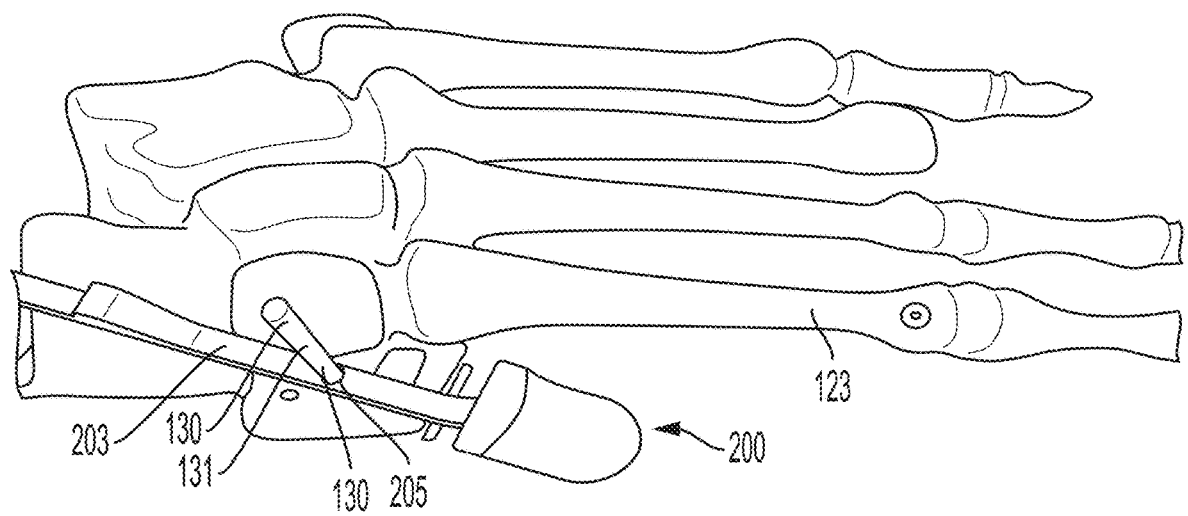
FIG. 2 is a top plan view of a wire guide engaging a bone.
Figure 3:
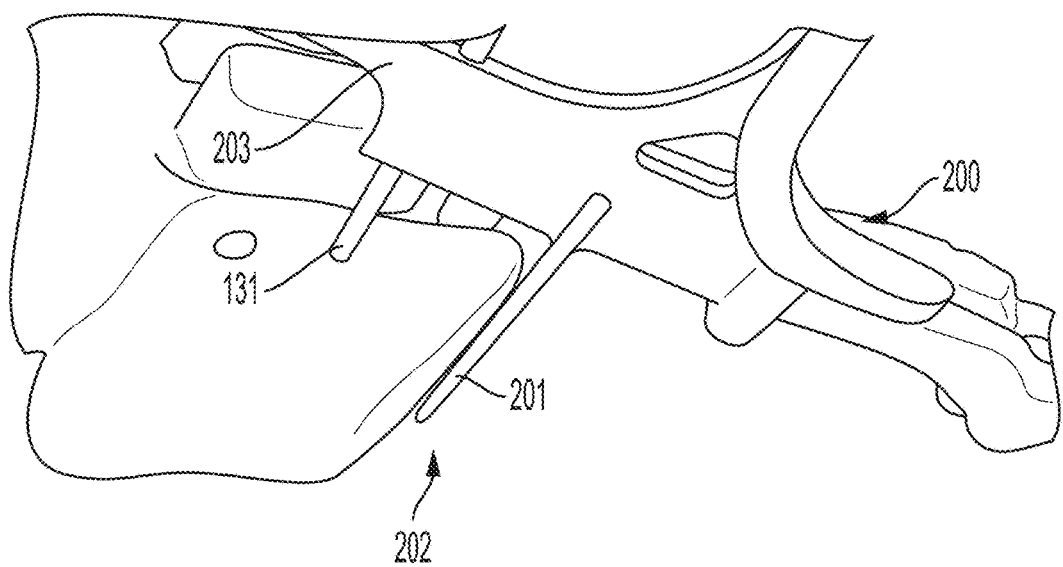
FIG. 3 is a side view of a portion of the wire guide and bone of FIG. 2.
Figure 4:
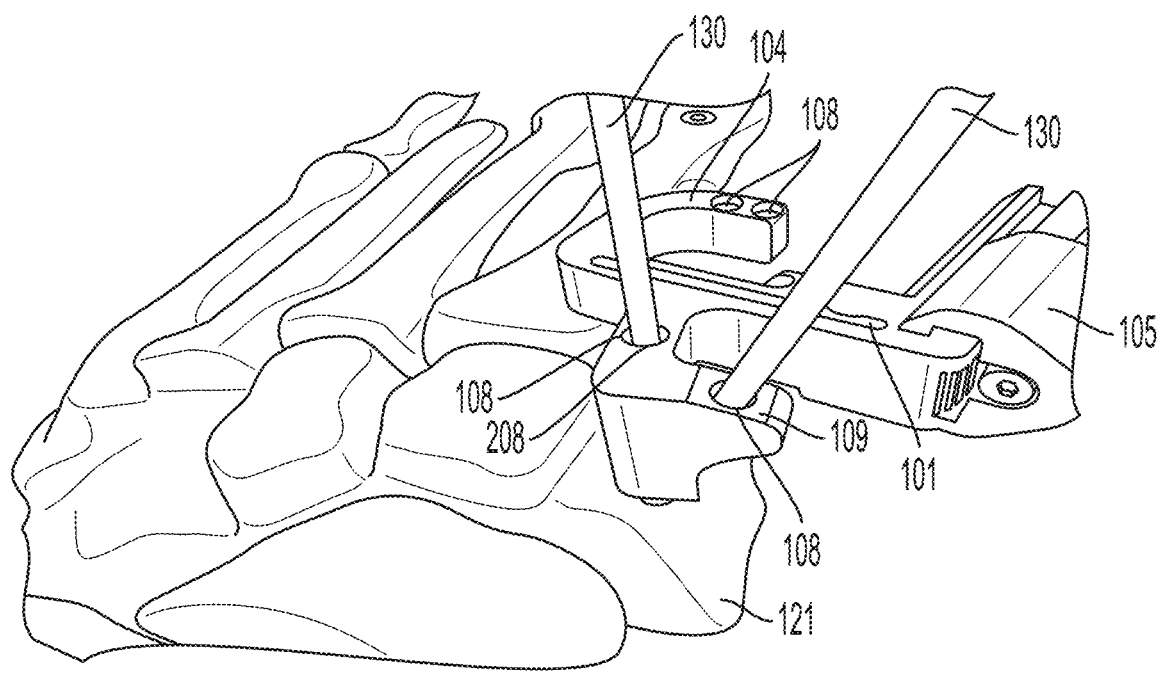
FIG. 4 is a perspective view of the cut guide of FIG. 1 being connected to a first bone portion and a second bone portion.
Figure 5:
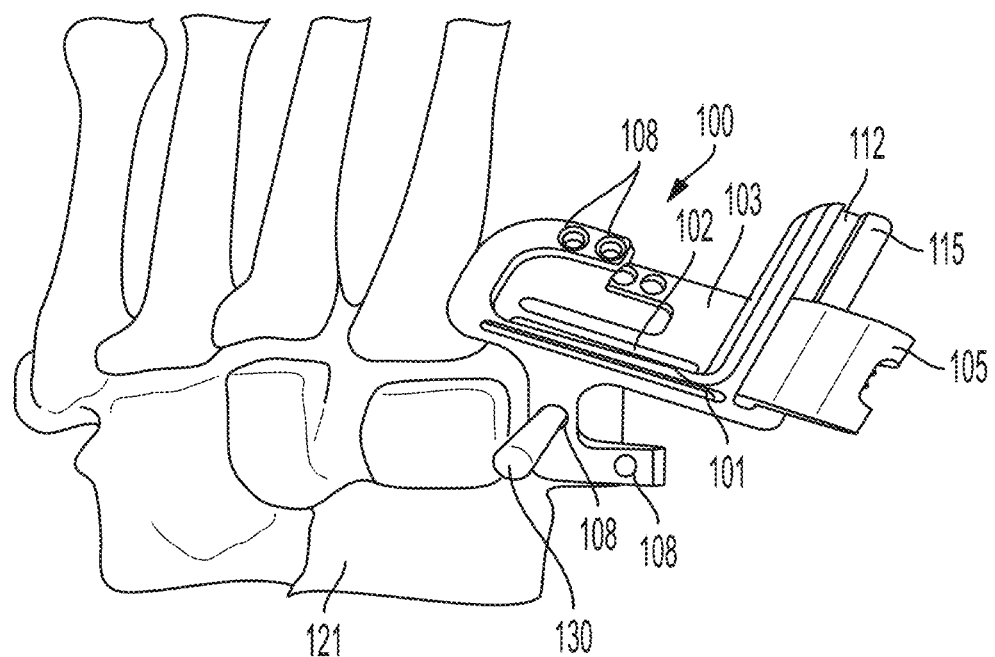
FIG. 5 is a top plan view of the cut guide of FIG. 1 connected to the bone via one wire.
Figure 6:
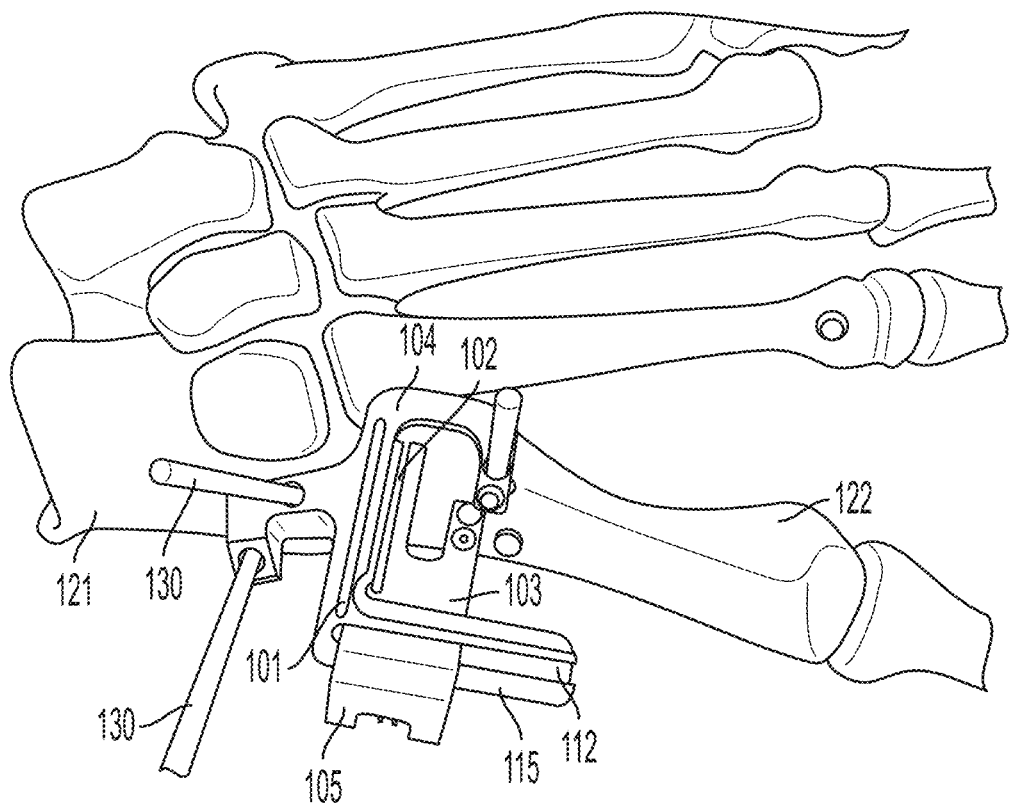
FIG. 6 is a top view of the cut guide of FIG. 5 with a second wire connecting the cut guide to the bone.
Figure 7:
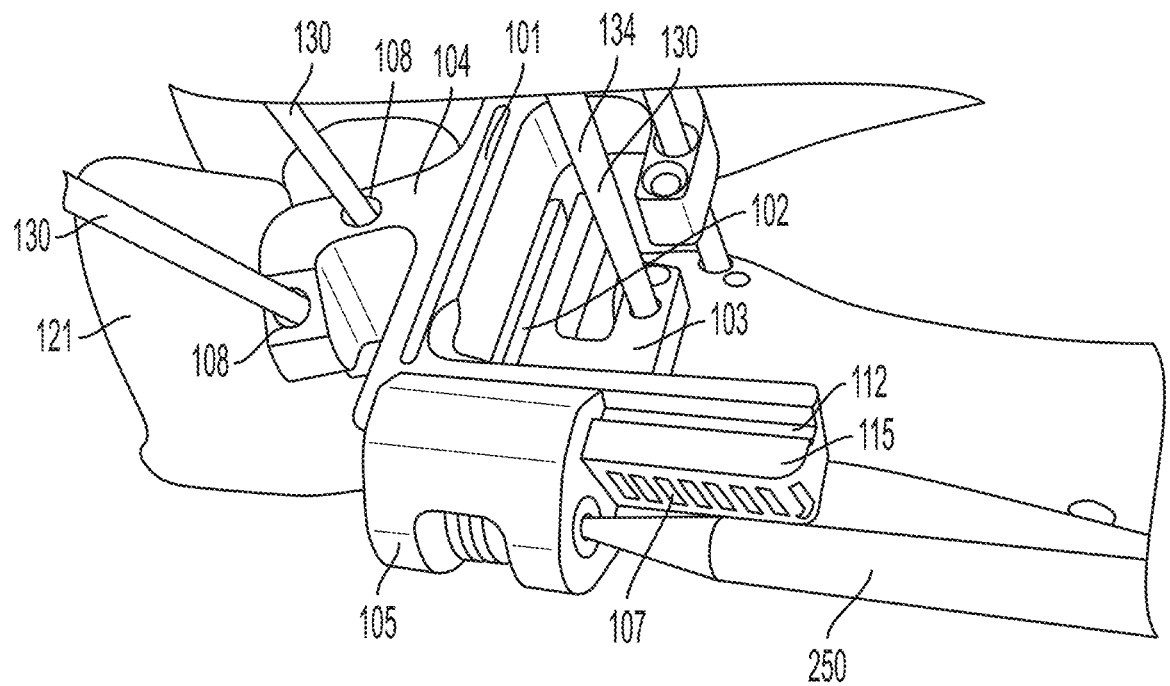
FIG. 7 is a perspective view of the cut guide of FIG. 6 with a third wire connected to the second bone portion.
Figure 8:
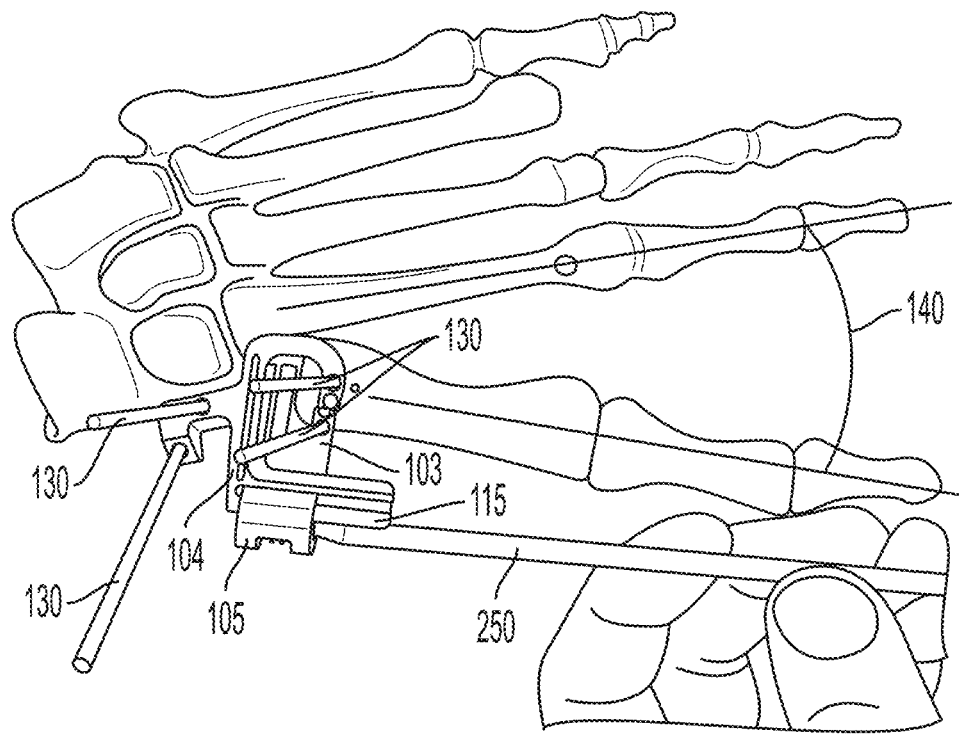
FIG. 8 is a top view of the cut guide of FIG. 7 showing an angle between two metatarsals.
Figure 9:
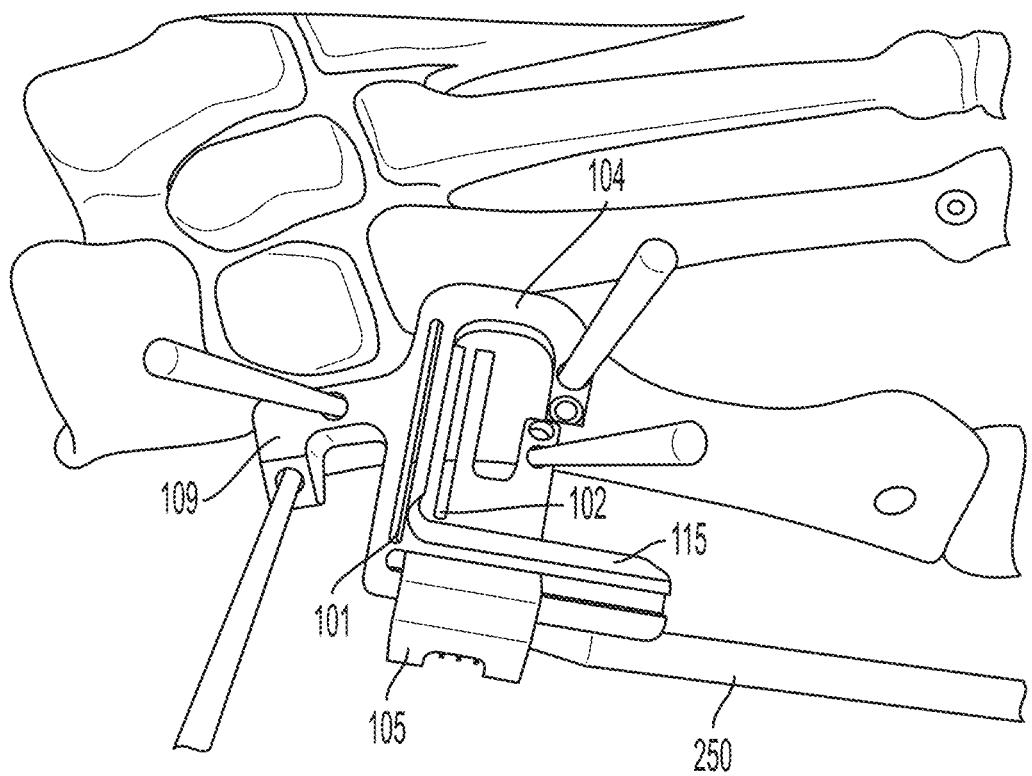
FIG. 9 is a top view of the cut guide of FIG. 8 with a compression-distraction portion thereof engaged to adjust an angle of the first and second metatarsals.
Figure 10:
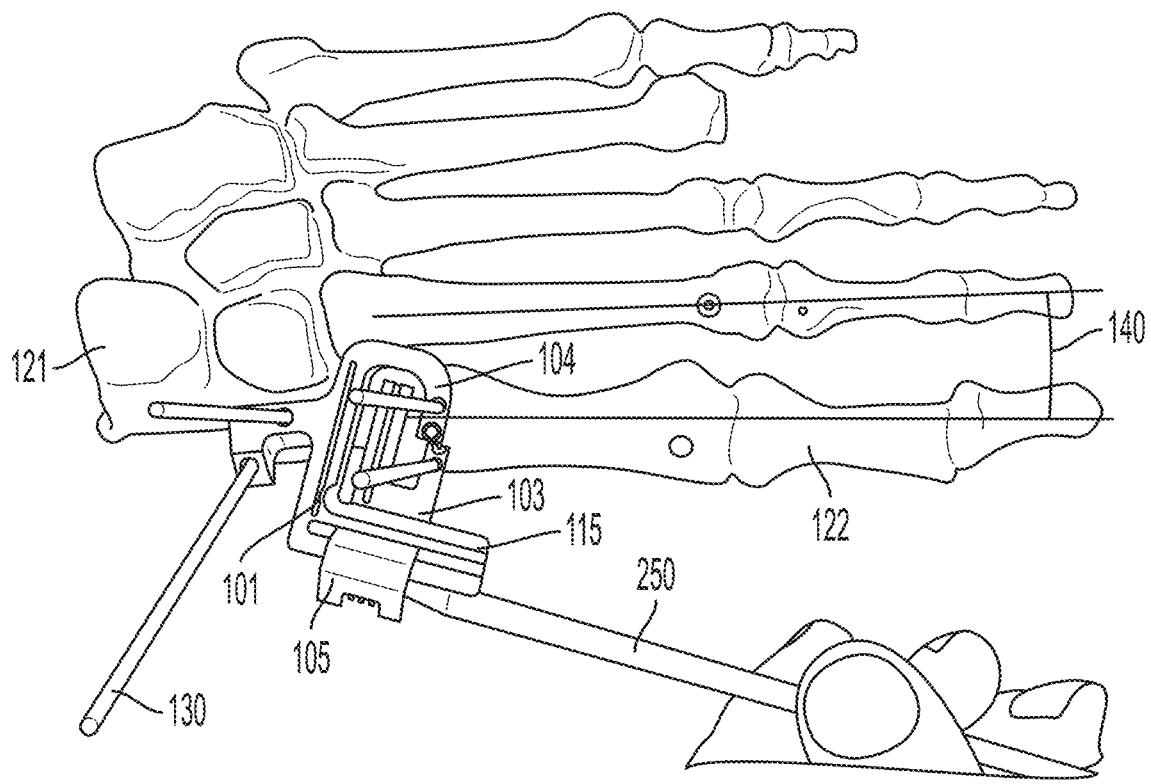
FIG. 10 is a top view of the cut guide of FIG. 9 with the first and second metatarsals aligned relative to each other in a desired position.
Figure 11:
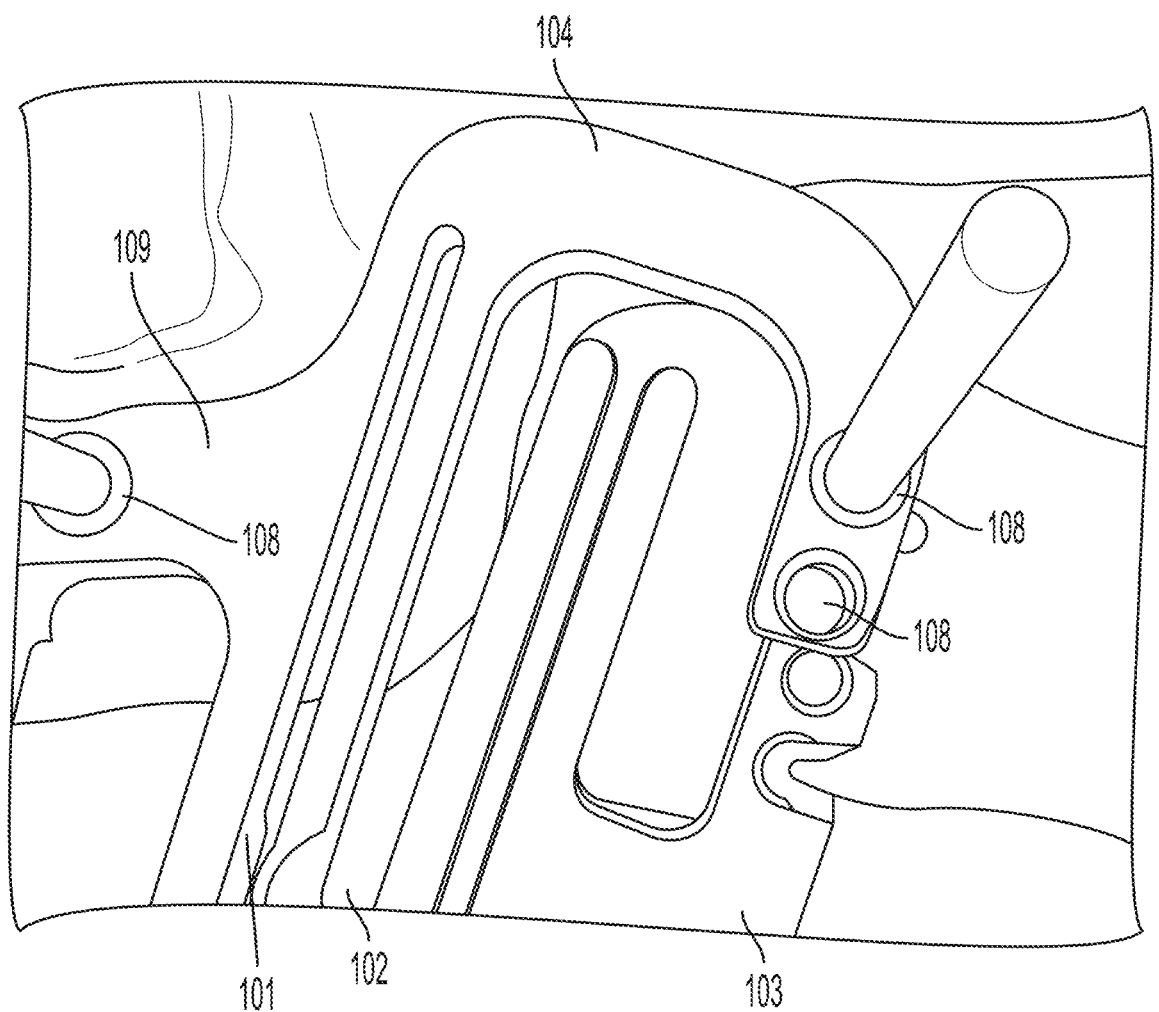
FIG. 11 is a top view of the bone cut guide of FIG. 10 in a position for cutting of first and second bone portions.

With reference to FIGS. 2-3, a wire guide 200 has a body 203, a bore hole 205, and an arm 201. Wire guide 200 is depicted with arm 201 positioned within a joint space 202 of a joint 204 between medial cuneiform bone 121 and first metatarsal bone 122 (FIG. 1).

Figure 12:
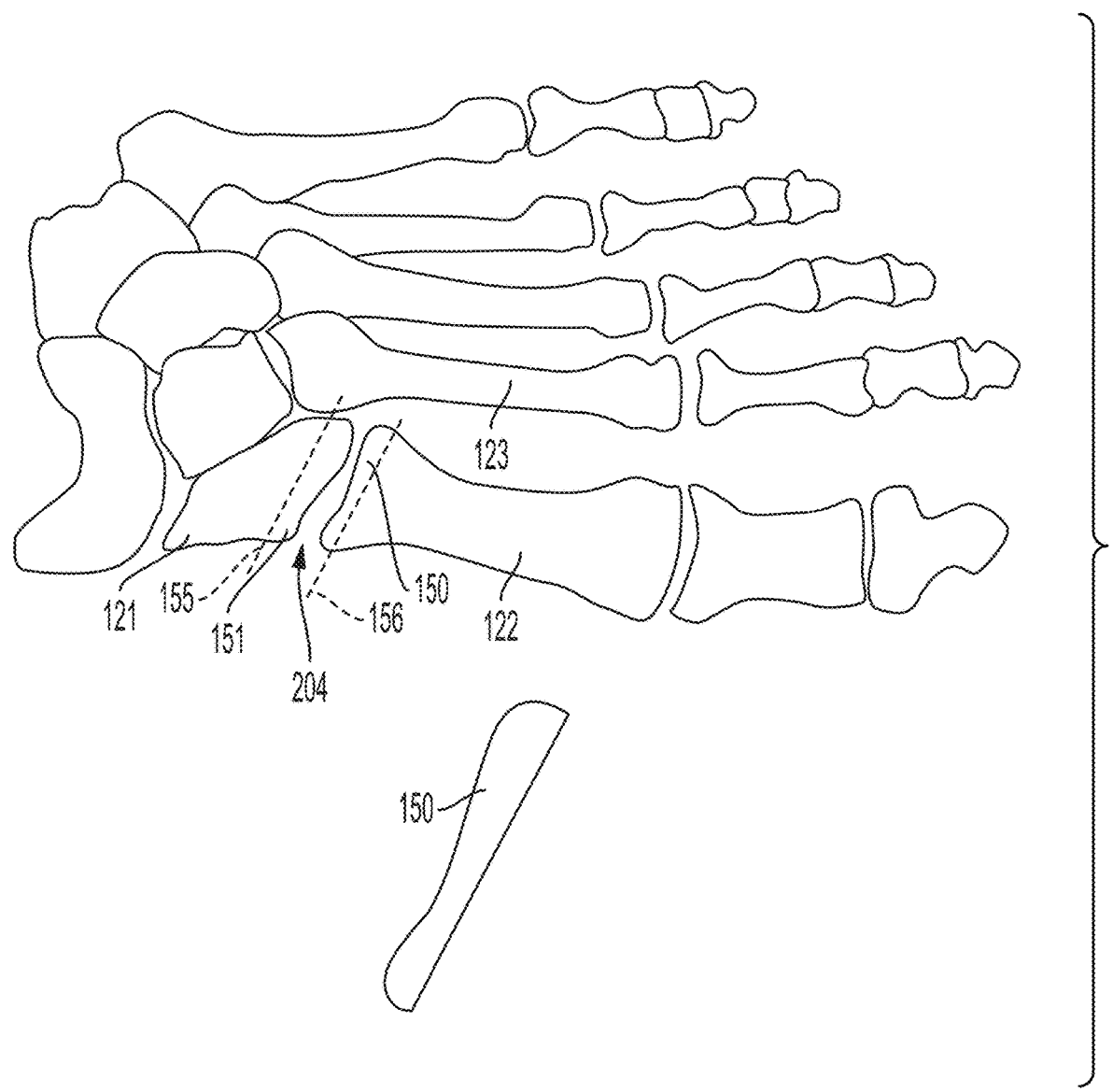
FIG. 12 is a schematic view of two bone portions removed as per the bone cut guide of FIG. 11.
Figure 13:
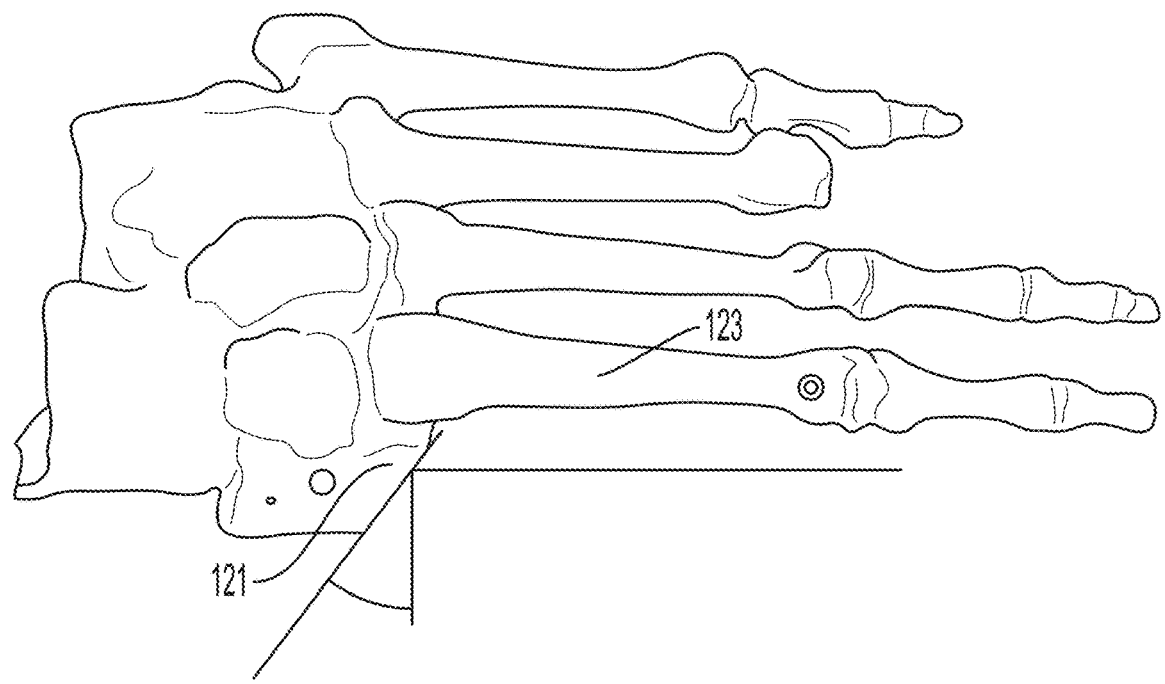
FIG. 13 is a top view of a foot showing an angle of obliquity.
Figure 14:
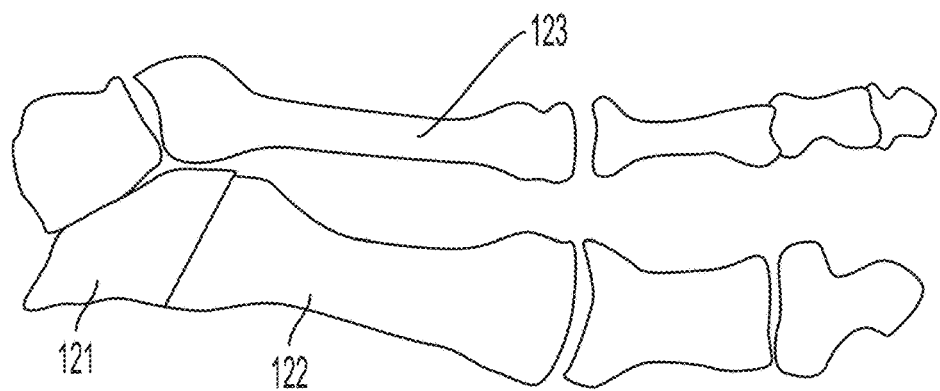
FIG. 14 is a schematic view of two metatarsals in a corrected position.

With reference to FIGS. 12-14, an angle of obliquity is depicted with first metatarsal bone 122 removed in FIG. 13, for use of illustration. First metatarsal bone 122 and a medial cuneiform bone 121 are depicted with a first bone wedge 150 removed from first metatarsal bone 122, and a second bone wedge 151 removed from medial cuneiform bone 121 in FIG. 12. A cuneiform cut 155 and a metatarsal cut 156 may be approximately parallel as depicted, for example, in FIG. 12. The resulting bone surfaces (FIG. 14) after first bone wedge 150 and second bone wedge 151 have been removed may, for example, be planar surfaces or further machined to be planar surfaces. Bone wedge 150 is depicted as having a thicker end and a thinner end, with the thicker end being bone removed from a lateral side of first metatarsal bone 122 and the thinner section being bone removed from a medial side of first metatarsal bone 122. In another embodiment, a bone material amount removed in second wedge 151 may be, for example, greater than a bone material amount removed in first bone wedge 150.

With reference to FIGS. 1-11 wire guide 200 (FIGS. 2-3) and cut guide 100 (FIGS. 1 and 4-11) are depicted for use in correcting the angle of obliquity between metatarsal bones (e.g. first metatarsal bone 122) and cuneiform bones (e.g., medial cuneiform bone 121). In an example, arm 201 of wire guide 200 is placed within joint space 202 to capture features of the joint such as obliquity, peaks and valleys. Wire guide 200 contains bore 205 for placing a landmark guide wire or a k-wire 131 of k-wires 130 into a bone (e.g., medial cuneiform bone 121) that can be used as a reference. Wire guide 200 establishes an initial k-wire position, and an inserted first k-wire (e.g., k-wire 131) is used to establish a cut distance. At this point, if a cut angle is known, a blocking k-wire (not shown) may be inserted into the bone (e.g., first metatarsal 122) to establish cut distance and angle. The blocking k-wire may be placed parallel to the first k-wire (e.g., outside guide 200 but parallel to a longitudinal dimension thereof) to stop rotation of guide 200 about the installed k-wire (e.g., k-wire 131) in a direction toward the second k-wire (not shown). However, if cut angle is yet to be determined, only one k-wire (e.g., k-wire 131) is used to allow rotation of guide 200. Selection of reference points for positioning cut guide 100 may be selected to, for example, remove more bone material from cuneiform bone 121 rather than from metatarsal bone 122.

With continued reference to FIGS. 1-11, wire guide 200 (FIGS. 2-3) is removed and cut guide 100 is placed on k-wire 131, for example, such that wire 131 is received in a bore 208 of bores 108. If a cut angle is known, cut guide 100 is placed onto two k-wires, such that the wires (e.g., wires 130) are received in bores (e.g., bores 108) of cut guide 100. For example, a first k-wire (e.g., wire 131) may control a longitudinal position along a longitudinal dimension of first metatarsal 122 and a second wire, such as a second k-wire 132 may be received through a second bore 209 of bores 108 to control a rotation of cut guide 100. Additional wires may be used to inhibit undesired positional and rotational movement of cut guide 100 relative to the bones (e.g. medial cuneiform bone 121 and first metatarsal bone 122), including upward drift.

Continuing to refer to FIGS. 1, and 4-11, if only one k-wire (e.g., k-wire 131) is used to connect cut guide 100 to cut guide 100 may be used (e.g., rotated about k-wire 131) to establish a cut angle, as desired by a surgeon. Cut guide 100 may be placed at a predetermined position with respect to the peaks and valleys of joint 204 such that first cut slot 101 which may guide removal of bone from medial cuneiform bone 121 removes a minimal amount. Positioning cut guide 100 may be made to, for example, remove a minimal amount of bone from first metatarsal bone 122, as well. A second k-wire (e.g., k-wire 132) may be connected to cut guide 100 (e.g., via second bore 209) once a desired angle is established (e.g., as set by a surgeon).

Referring to FIGS. 4-7, the position of one hole/bore (e.g., bore 209) on cut guide 100 may be, for example, at an angle relative to a first bore (e.g., bore 208). By inserting at least two k-wires (e.g., k-wire 131 and k-wire 132) at angles to each other via bore 208 and bore 209, upward drift of cut guide 100 may be inhibited or prevented during cutting. A third k-wire (e.g, a k-wire 133) may be connected through cut guide 100 to, for example, a lateral edge of first metatarsal bone 122. A final k-wire (e.g., a k-wire 134) may be placed into, for example, a medial aspect of first metatarsal bone 122, securing the k-wire to second member 103.

Still referring to FIGS. 7-10, mobile metatarsal cutting portion 103 may be actuated using, for example, power screw 106. Other actuation means may be used to translate mobile metatarsal cutting portion 103 relative to cut guide body 104. By actuating metatarsal adjustment screw 106, the metatarsal cutting portion 103 (e.g., distal metatarsal cutting slot 102 thereof) of cut guide 100 is advanced distally. Distal advancement of the medial side of first metatarsal bone 122 while the lateral side is fixed places a moment on the metatarsal (e.g. first metatarsal bone 122), causing an intermetatarsal angle 140 to decrease. As metatarsal cutting portion 103 advances distally, both proximal cuneiform cutting slot 101, and distal metatarsal cutting slot 102 remain parallel.

Further referring to FIGS. 11-14, once intermetatarsal angle 140 angle is reduced to a desired angle and first metatarsal bone 122 is in a desired position, parallel saw cuts can be made using proximal cuneiform cutting slot 101 and distal metatarsal cutting slot 102. Both slots are parallel and are configured (e.g. shaped and dimensioned) to, for example, remove more bone material from the lateral side of cuneiform bone 121 and the lateral side of first metatarsal bone 122. In another example, cut guide 100 positioning is selected to remove material from medial cuneiform bone 121 and first metatarsal bone 122 in parallel configurations with bone removal creating parallel surfaces for bone alignment (i.e. alignment of medial cuneiform bone 121 and first metatarsal bone 122), where such removal is necessary to correct the angle of obliquity. With reference to FIGS. 11-14, once the cuts have been made, cut guide 100 may be removed and the bones (i.e. medial cuneiform bone 121 and first metatarsal bone 122) brought into apposition for placement of hardware. However, cut guide 100 may remain connected to assist with hardware placement. By removing the k-wire on the lateral edge of first metatarsal bone 122, power screw 106 may, for example, be turned in the opposite direction, advancing mobile metatarsal cutting portion 103 towards cut guide body 104 until bones are in apposition and compression is applied.

Continuing to refer to FIGS. 11-14, cut guide 100 establishes the angle of the cuts prior to performing a cut and provides for parallel cuts to the bones (e.g. medial cuneiform bone 121 and first metatarsal bone 122), allowing medial cuneiform bone 121 and first metatarsal bone 122 to be set at the desired angle. By establishing the angle prior to performing the cut, joint correction is performed first. By doing so, intermetatarsal angle 140 is adjusted before the cut, and cut guide 100 provides for two parallel cuts (e.g. one to medial cuneiform bone 121 and one to first metatarsal bone 122) removing a fixed amount of bone before first metatarsal bone 122 is fused/connected to medial cuneiform bone 121 at the adjusted intermetatarsal angle. The bone surfaces after the cut are parallel and may be, for example, approximately flush when fused. Since the bone was adjusted prior to the cut, fusion does not affect the adjusted intermetatarsal angle (e.g., intermetatarsal angle 140) and first metatarsal bone 122 remains positioned at the adjusted intermetatarsal angle.

Although the slots (e.g., cuneiform cutting slot 101 and distal metatarsal cutting slot 102) are described above as being parallel to achieve parallel saw cuts, such slots may be substantially or approximately parallel such that the bone surfaces of the bones (e.g., first metatarsal bone 122 and medial cuneiform bone 121) to be fused are parallel enough after cutting via such slots to allow the fusion of the bones after the desired correction of the intermetatarsal angle (e.g., intermetatarsal angle 140).

Cut guide 100 may be reversed so that the majority of medial bone is removed from the cuneiform bone rather than the metatarsal bone.

In other embodiments, the initial k-wire hole may be a slot to allow for customization of cut depth.

The process of correcting frontal plane rotation occurs prior to placement of distal k-wires.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

We claim:

1. A method for use in aligning bones, comprising:
    inserting a joint arm of a guide between a first bone and a second bone;
    inserting a first wire through a guide aperture of the guide into the first bone;
    removing the guide from the first bone and the first wire;
    attaching a first portion of a bone cut guide to the first bone by receiving the first wire in a first aperture of the bone cut guide; and
    attaching a second portion of the bone cut guide to the second bone by receiving a second wire in a second aperture of the bone cut guide and inserting the second wire in the second bone.

2. The method of claim 1 further comprising receiving a third wire in a third aperture of the first portion to connect the first portion to the first bone to inhibit a rotation of the first portion about the first wire.

3. The method of claim 1 further comprising moving the first portion and the second portion relative to each other to adjust an angle of a longitudinal dimension of the first bone relative to a second longitudinal dimension of the second bone.

4. The method of claim 1 further comprising moving the first portion and the second portion relative to each other to adjust an angle of a longitudinal dimension of the second bone relative to a second longitudinal dimension of a third bone.

5. The method of claim 1 further comprising cutting the first bone through a first cutting slot of the first portion and cutting the second bone through a second cutting slot of the second portion wherein the first cut slot and the second cut slot have longitudinal dimensions substantially parallel to each other.

6. The method of claim 1 further comprising moving the first portion and the second portion using a compression-distraction fixture connected to the first portion and the second portion for moving the first portion relative to the second portion.

7. The method of claim 6 wherein the moving the first portion and the second portion comprises a user advancing a screw of the compression-distraction fixture to engage a rack to cause the second portion to distally move away from the first bone.

8. The method of claim 7 wherein the moving the second portion distally causes a distal advancement of a medial side of the second bone and a lateral side of the second bone is held in place by the second wire to cause an angle between a longitudinal axis of the second bone and a longitudinal axis of a third bone to decrease.

9. The method of claim 1 further comprising aligning a longitudinal axis of a longitudinal dimension of a first arm of the first portion substantially parallel to a longitudinal axis of a longitudinal dimension of the first bone.

10. The method of claim 1 wherein the inserting the joint arm of the guide between the first bone and the second bone comprises the joint arm of the guide contacting the first bone to align the guide to locate the guide aperture and the first wire, and further comprising rotating the cut guide about the wire to a desired position.

11. The method of claim 10 further comprising receiving a third wire in a third aperture of the first portion to connect the first portion to the first bone to inhibit a rotation of the first portion about the first wire.

* * * * *